US011612761B2

(12) United States Patent
Basiri et al.

(10) Patent No.: US 11,612,761 B2
(45) Date of Patent: Mar. 28, 2023

(54) TRAINING ARTIFICIAL INTELLIGENCE MODELS FOR RADIATION THERAPY

(71) Applicant: VARIAN MEDICAL SYSTEMS INTERNATIONAL AG, Palo Alto, CA (US)

(72) Inventors: Shahab Basiri, Siuntio (FI); Mikko Hakala, Rajamäki (FI); Esa Kuusela, Espoo (FI); Elena Czeizler, Helsinki (FI)

(73) Assignee: VARIAN MEDICAL SYSTEMS INTERNATIONAL AG, Palo Alto, CA (US)

( * ) Notice: Subject to any disclaimer, the term of this patent is extended or adjusted under 35 U.S.C. 154(b) by 282 days.

(21) Appl. No.: 17/124,249

(22) Filed: Dec. 16, 2020

(65) Prior Publication Data

US 2022/0184419 A1 Jun. 16, 2022

(51) Int. Cl.
*A61N 5/10* (2006.01)
*G06N 3/08* (2023.01)
(52) U.S. Cl.
CPC ............. *A61N 5/1038* (2013.01); *G06N 3/08* (2013.01); *A61N 2005/1041* (2013.01)
(58) Field of Classification Search
CPC ............. A61N 5/10; A61N 5/1038; A61N 2005/1041; G06N 3/08; G16H 20/40
See application file for complete search history.

(56) References Cited

U.S. PATENT DOCUMENTS

| 2019/0333623 A1* | 10/2019 | Hibbard | ............. G06N 3/08 |
| 2022/0296923 A1* | 9/2022 | Peltola | ............. A61N 5/103 |
| 2022/0296924 A1* | 9/2022 | Peltola | ............. A61N 5/1038 |

* cited by examiner

Primary Examiner — Jurie Yun
(74) Attorney, Agent, or Firm — Foley & Lardner LLP

(57) ABSTRACT

Disclosed herein are systems and methods for iteratively training artificial intelligence models using reinforcement learning techniques. With each iteration, a training agent applies a random radiation therapy treatment attribute corresponding to the radiation therapy treatment attribute associated with previously performed radiation therapy treatments when an epsilon value indicative of a likelihood of exploration and exploitation training of the artificial intelligence model satisfies a threshold. When the epsilon value does not satisfy the threshold, the agent generates, using an existing policy, a first predicted radiation therapy treatment attribute, and generates, using a predefined model, a second predicted radiation therapy treatment attribute. The agent applies one of the first predicted radiation therapy treatment attribute or the second predicted radiation therapy treatment attribute that is associated with a higher reward. The agent iteratively repeats training the artificial intelligence model until the existing policy satisfies an accuracy threshold.

20 Claims, 9 Drawing Sheets

TRAINING ARTIFICIAL INTELLIGENCE MODELS FOR RADIATION THERAPY

TECHNICAL FIELD

This application relates generally to generating, training, and operating artificial intelligence (AI) computer models to predict radiation therapy treatment procedures.

BACKGROUND

Radiation therapy treatment planning (RTTP) is a complex process that contains specific guidelines, protocols and instructions adopted by different medical professionals, such as the clinicians, the manufacturers of the medical device, the treating physicians, and the like. Due to the extreme nature of radiation emitted from the radiation therapy machine, it is imperative that treatment attributes are precisely calculated and followed. Treatment attributes, as used in the context of RTTP, refers to various attributes of how the patient's treatment is implemented including attributes of a radiation therapy machine while the patient is receiving the prescribed radiotherapy dose and how the dosage is delivered to the patient's organs. For instance, the prescribing physician may identify a source location (e.g., patient's organ to be treated or tumor to be eradicated) and a corresponding dosage. As a result, other parties (e.g., clinicians or machine manufacturer) may determine positioning attributes (e.g., angles) of the gantry and the patient on the couch and how the dosage should be delivered to the patient to receive optimum treatment.

Conventionally, identifying and applying guidelines to implement radiation therapy treatment are performed by the clinician/technician. For instance, selecting a treatment attribute (e.g., optimizing dose-volume histogram (DVH) objectives and dose distribution planning) for a patient has been delegated to clinicians who use their subjective understanding and skills. For instance, a human planner may interact with a plan generation interface for IMRT treatments and may manually modify the plan (e.g., dosages received by different organs) until an acceptable plan is achieved. However, this conventional method is inefficient because it is time consuming, tedious, error-prone, and heavily relies on the clinician's subjective understanding and skills.

In order to remedy the above-described problem, many medical professionals utilize AI-enabled software solutions. For instance, a medical professional may use these software solutions to determine treatment attributes and the dosage received by different organs. These software solutions use AI models trained based on previously performed radiation therapy treatments, such as RTTPs and how patient treatments were implemented (sometimes referred to as the training dataset and/or ground truth data). The AI models may uncover hidden patterns/solutions and reconfigure themselves. However, conventional AI training methods have faced technical shortcomings. For instance, conventional training methods require a large number of training data points and are computationally intensive, costly, and require a long training period.

SUMMARY

For the aforementioned reasons, there is a desire for a computer model to generate treatment attributes using methods and systems that are no longer dependent on the technician's subjective interpretation or conventional AI training methods. For the aforementioned reasons, there is a desire for an improved AI modeling/training technique that does not require extensive training datasets and is timely, computationally efficient, and cost efficient. What is desired is an AI modeling/training technique that is more efficient and produces results that are more accurate without needing a large training dataset.

The methods and systems described herein address the above-described technical shortcomings by providing a training system that does not require a large number of ground truth datasets and provides accurate results. The described AI training methods/systems allow a server to train an AI model using fewer data points, such that the trained AI model can ingest RTTP data and predict treatment attributes.

In an embodiment, a method of training an artificial intelligence model using reinforcement learning, the method comprises iteratively training, by a server, the artificial intelligence model using a training dataset comprising a set of radiation therapy treatment attributes associated with previously performed radiation therapy treatments to predict a corresponding set of radiation therapy treatment attributes, wherein with each iteration the server: applies a random radiation therapy treatment attribute corresponding to the radiation therapy treatment attribute associated with previously performed radiation therapy treatments when an epsilon value indicative of a likelihood of exploration and exploitation training of the artificial intelligence model satisfies a threshold; and when the epsilon value does not satisfy the threshold, the server generates, using an existing policy, a first predicted radiation therapy treatment attribute, and generates, using a predefined computer model, a second predicted radiation therapy treatment attribute, wherein the server applies one of the first predicted radiation therapy treatment attribute or the second predicted radiation therapy treatment attribute that is associated with a higher reward, wherein the server iteratively repeats training the artificial intelligence model until the existing policy satisfies an accuracy threshold.

In another embodiment, a system for training an artificial intelligence model using reinforcement learning comprises one or more processors; and a non-transitory memory to store computer code instructions, the computer code instructions when executed cause the one or more processors to: iteratively train the artificial intelligence model using a training dataset comprising a set of radiation therapy treatment attributes associated with previously performed radiation therapy treatments to predict a corresponding set of radiation therapy treatment attributes, wherein with each iteration the one or more processors: apply a random radiation therapy treatment attribute corresponding to the radiation therapy treatment attribute associated with previously performed radiation therapy treatments when an epsilon value indicative of a likelihood of exploration and exploitation training of the artificial intelligence model satisfies a threshold; and when the epsilon value does not satisfy the threshold, the one or more processors: generate, using an existing policy, a first predicted radiation therapy treatment attribute, and generate, using a predefined computer model, a second predicted radiation therapy treatment attribute, wherein the one or more processors apply one of the first predicted radiation therapy treatment attribute or the second predicted radiation therapy treatment attribute that is associated with a higher reward, wherein the server iteratively repeats training the artificial intelligence model until the existing policy satisfies an accuracy threshold.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

DETAILED DESCRIPTION

Figure 1:
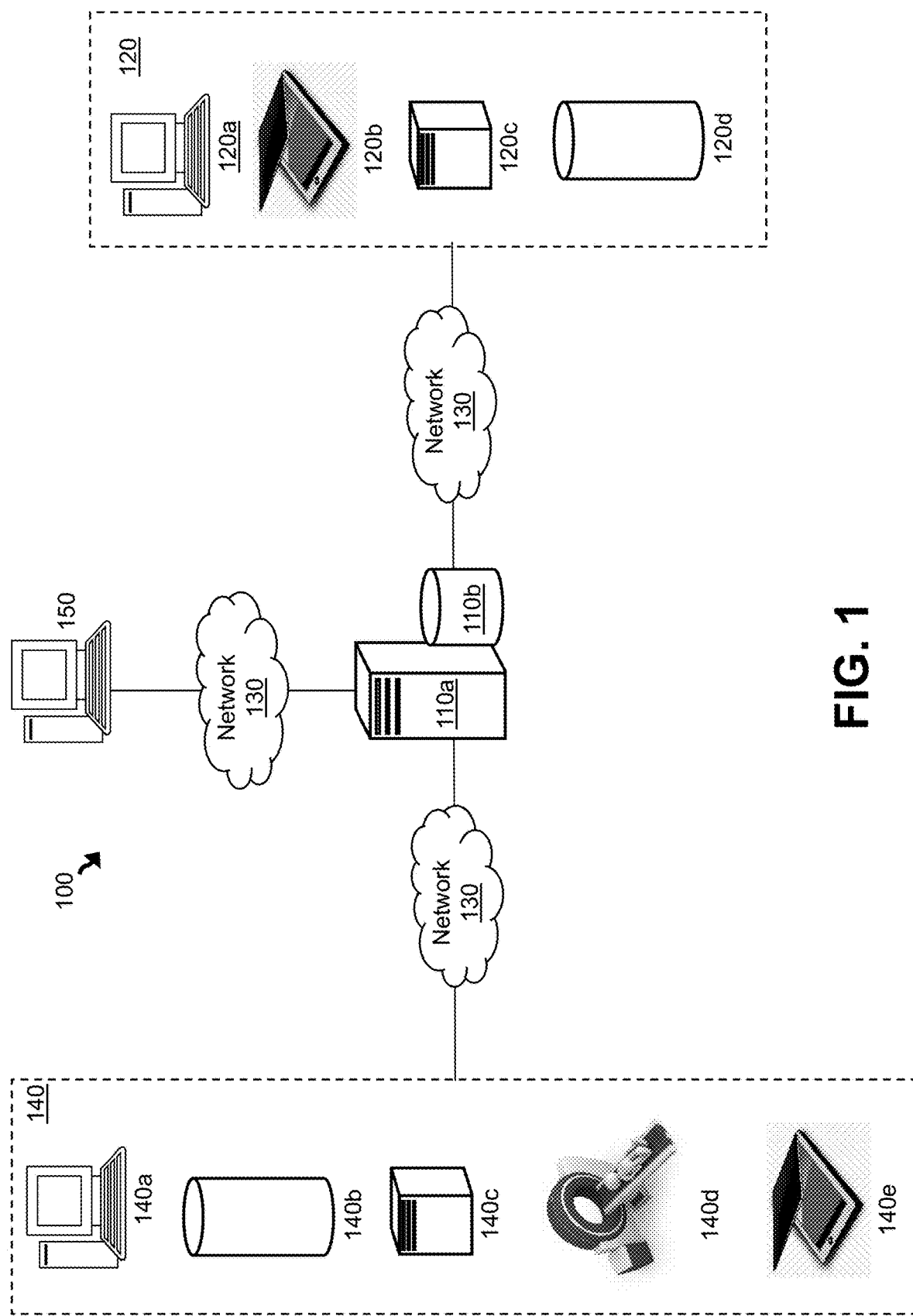
FIG. 1 illustrates components of an AI-enabled RTTP optimization system, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

As will be described below, a central server (referred to herein as the analytics server) can retrieve and train an AI model using various methods described herein to identify attributes of a patient's treatment. FIG. 1 is a non-limiting example of components of a system in which the analytics server operates. The analytics server may utilize features described in FIG. 1 to retrieve data, train an AI model, and execute the trained model to generate/display treatment attributes, such as field geometry.

FIG. 1 illustrates components of an AI-enabled RTTP optimization system 100. The system 100 may include an analytics server 110a, system database 110b, electronic data sources 120a-d (collectively electronic data sources 120), end-user devices 140a-e (collectively end-user device 140), and an administrator computing device 150. The above-mentioned components may be connected to each other through a network 130. The examples of the network 130 may include, but are not limited to, private or public LAN, WLAN, MAN, WAN, and the Internet. The network 130 may include both wired and wireless communications according to one or more standards and/or via one or more transport mediums.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The system 100 is not confined to the components described herein and may include additional or other components, not shown for brevity, which are to be considered within the scope of the embodiments described herein.

The analytics server 110a may generate and display an electronic platform configured to use various computer models (including artificial intelligence models) to identify and display RTTP. The electronic platform may include graphical user interfaces (GUI) displayed on each electronic data source 120, the administrator computing device 150, and/or end-user devices 140. An example of the electronic platform generated and hosted by the analytics server 110a may be a web-based application or a website configured to be displayed on different electronic devices, such as mobile devices, tablets, personal computer, and the like. In a non-limiting example, a physician operating the physician device 120b may access the platform, input patient attributes and other data, and further instruct the analytics server 110a to generate an optimized RTTP. The analytics server 110a may then utilize the methods and systems described herein to generate an RTTP and display the results on the end-user devices (e.g., radiation therapy machine 140d). In some configurations, the analytics server 110a may display the RTTP on the physician device 120b itself as well.

The analytics server 110a may host a website accessible to users operating any of the electronic devices descried herein (e.g., end-users), where the content presented via the various webpages may be controlled based upon each particular user's role or viewing permissions. The analytics server 110a may be any computing device comprising a processor and non-transitory machine-readable storage capable of executing the various tasks and processes described herein. Non-limiting examples of such computing devices may include workstation computers, laptop computers, server computers, and the like. While the system 100 includes a single analytics server 110a, in some configurations, the analytics server 110a may include any number of computing devices operating in a distributed computing environment.

The analytics server 110a may execute software applications configured to display the electronic platform (e.g., host a website), which may generate and serve various webpages to each electronic data source 120 and/or end-user devices 140. Different users may use the website to view and/or interact with the predicted results.

The analytics server 110a may be configured to require user authentication based upon a set of user authorization credentials (e.g., username, password, biometrics, cryptographic certificate, and the like). In such implementations, the analytics server 110a may access the system database 110b configured to store user credentials, which the analytics server 110a may be configured to reference in order to determine whether a set of entered credentials (purportedly authenticating the user) match an appropriate set of credentials that identify and authenticate the user.

The analytics server 110a may also store data associated with each user operating one or more electronic data sources 120 and/or end-user devices 140. The analytics server 110a may use the data to weigh interaction while training various AI models accordingly. For instance, the analytics server 110a may indicate that a user is a medical professional whose inputs may be monitored and used to train the AI or other computer models described herein.

In some configurations, the analytics server 110a may generate and host webpages based upon a particular user's role within the system 100. In such implementations, the user's role may be defined by data fields and input fields in user records stored in the system database 110b. The analytics server 110a may authenticate the user and may identify the user's role by executing an access directory protocol (e.g. LDAP). The analytics server 110a may generate webpage content that is customized according to the user's role defined by the user record in the system database 110b.

The analytics server 110a receives RTTP data (e.g., patient and treatment data) from a user (or retrieve from a data repository), analyzes the data, and displays the results on the electronic platform. For instance, in a non-limiting example, the analytics server 110a may query and retrieve medical images from the database 120d and combine the medical images with RTTP data received from a physician operating the physician device 120b. The analytics server 110a then uses various models (stored within the system database 110b) to analyze the retrieved data. The analytics server 110a then displays the results (e.g., RTTP including couch and gantry angles) via the electronic platform on the administrator computing device, the end-user devices 140, and/or the physician device 120b.

End-user devices 140 may be any computing device comprising a processor and a non-transitory machine-readable storage medium capable of performing the various tasks and processes described herein. Non-limiting examples of a network node may be a workstation computer, laptop computer, tablet computer, and server computer. In operation, various users may use end-user devices 140 to access the GUI operationally managed by the analytics server 110a. Specifically, the end-user devices 140 may include clinic computer 140a, clinic database 140b, clinic server 140c, a medical device, such as a CT scan machine, radiation therapy machine, and the like (140d), clinic device 140e.

The electronic data sources 120 may represent various electronic data sources that contain, retrieve, and/or input data associated with RTTP (e.g., patient data and treatment data). For instance, the analytics server 110a may use the clinic computer 120a, physician device 120b, server 120c (associated with a physician and/or clinic), and database 120d (associated with the physician and/or the clinic) to retrieve/receive RTTP data associated with a particular patient's treatment plan.

The administrator computing device 150 may represent a computing device operated by a system administrator. The administrator computing device 150 may be configured to display data retrieved, RTTP generated by the analytics server 110a (e.g., various analytic metrics and field geometry) where the system administrator can monitor various models utilized by the analytics server 110a, review feedback, and modify various thresholds/rules described herein.

In operation, a physician may access an application executing on the physician device 120b and input RTTP data (e.g., patient information, patient diagnosis, radiation therapy treatment attributes). The analytics server 110a then uses a patient identifier to query patient data (e.g., patient anatomy and/or medical images) from the electronic data sources 120. The analytics server may then identify a clinic associated with the patient (e.g., clinic performing the treatment) and retrieve one or more files associated with treatment templates and clinic rules. The analytics server 110a may then utilize the systems and methods described herein to generate an optimized RTTP and display the results onto the physician device 120b, clinic computer 140a, and the medical device 140d (e.g., a display screen of the radiation therapy machine).

The analytics server 110a may generate the optimized RTTP based on patient data and the patient's treatment requirements. The analytics server 110a may execute a trained AI model that has been previously trained using the AI training methods described herein.

The analytics server 110a may be in communications (real time or near real time) with the medical device 140d, such that a server/computer hosting the medical device 140d can adjust the medical device 140d based on the RTTP generated by the analytics server 110a. For instance, the radiation therapy machine may adjust the gantry and couch based on angles and other attributes determined by the analytics server 110a.

Figure 2A:
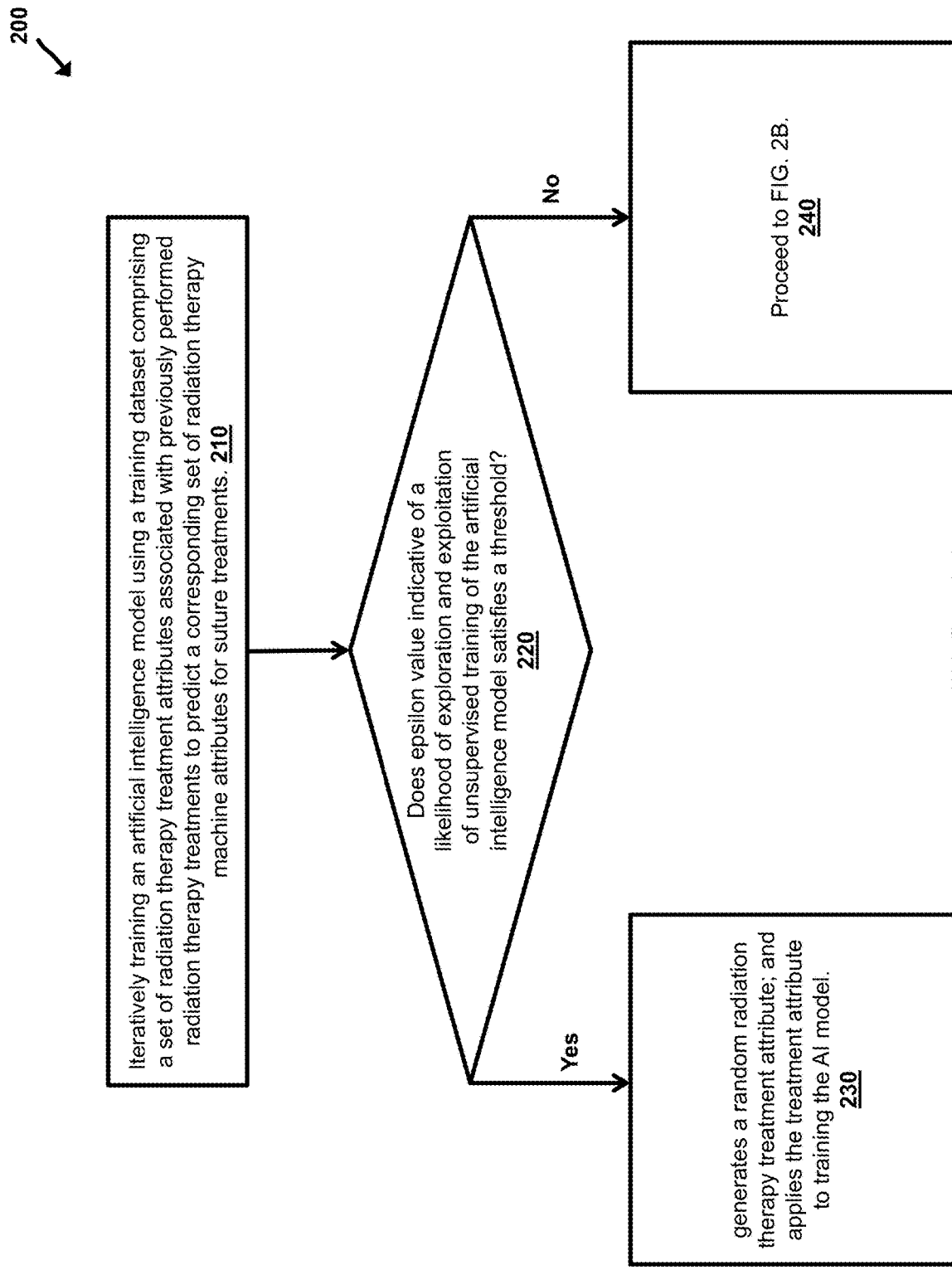
FIGS. 2A-B illustrate a flow diagram of a process executed in an AI-enabled RTTP optimization system, according to an embodiment.
Figure 2B:
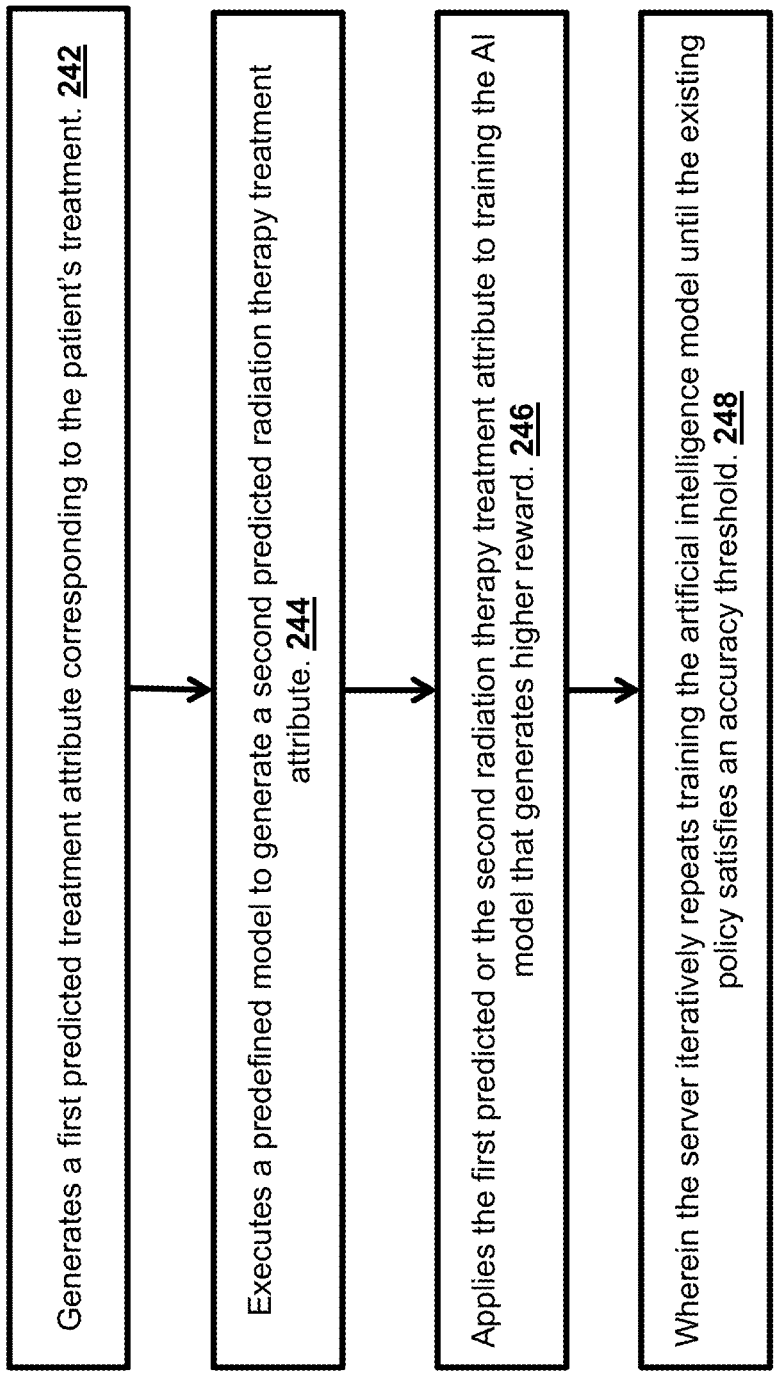

FIGS. 2A-B illustrate a flow diagram of a process executed in an RTTP optimization system, according to an embodiment. The method 200 includes steps 210-248. However, other embodiments may include additional or alternative execution steps, or may omit one or more steps altogether. The method 200 is described as being executed by a server, similar to the analytics server described in FIG. 1. However, one or more steps of method 200 may also be executed by any number of computing devices operating in the distributed computing system described in FIG. 1. For instance, one or more user computing devices may locally perform part or all the steps described in FIGS. 2A-B. Moreover, an "agent" referring to the learner or the trainer (e.g., the analytics server training the AI model or the AI model itself) may perform one or more steps discussed herein.

At step 210, the analytics server may iteratively train an artificial intelligence model using a training dataset comprising a set of radiation therapy treatment attributes associated with previously performed radiation therapy treatments. The analytics server may use the method 200 to train an artificial intelligence model, such that when executed, the trained AI model can predict various treatment attributes (e.g., tumor locations, field geometry, and/or machine attributes) for future patients. The analytics server may train the AI model using data associated with previously performed treatments. For instance, the analytics server may retrieve RTTP and/or other treatment data/attributes (e.g., data associated with how the treatment identified within the RTTP was implemented by different clinics) to train the AI model.

The analytics server may retrieve the above-described data from one or more clinics and/or may augment the data using third-party data. The analytic server may use the retrieved data as the aggregated ground truth data and use the data retrieved to train the AI model. While conventional AI training methods may use brute force techniques, the methods described herein (e.g., the method 200) may use the ground data in a limited way to decrease training time and increase efficiency. The methods and systems described herein may combine multiple training methods (e.g., reinforcement learning and supervised learning) in a particular way to increase training efficiency.

The analytics server may receive RTTP files associated with one or more previously treated patients. The RTTP files may include radiation-therapy-specific information associated with the previously treated patients. The RTTP files may refer to a file having data associated with a process in which a medical team (e.g., radiation oncologists, radiation therapist, medical physicists, and/or medical dosimetrists) plan the appropriate external beam radiotherapy or internal brachytherapy treatment techniques for a patient.

The RTTP may include a patient identifier, patient's electronic health data records, medical images (e.g., CT scans, 4D CT Scans, MRIs, and X-ray images), treatment-specific data (e.g., arc information or treatment type), target organ (e.g., specification and location data to identify the tumor to be eradicated). Additional examples may include non-target organs, dosage-related calculations (e.g., radiation dose distribution within an anatomical region of the patient), and radiation therapy machine specific recommendations (e.g., couch-gantry orientations and/or arc information).

The analytics server may use different patient identifiers within the RTTP files (or otherwise retrieved) to identify a particular patient and retrieve additional information regarding said patient. For instance, the analytics server may query one or more databases to identify medical data associated with the patient. The analytics server may query data associated with the patient's anatomy, such as physical data (e.g., height, weight, and/or body mass index) and/or other health-related data (e.g., blood pressure or other data relevant to the patient receiving radiation therapy treatment). The analytics server may also retrieve data associated with current and/or previous medical treatments received by the patient (e.g., data associated with the patient's previous surgeries).

The analytics server may analyze the data received and may generate additional queries accordingly. For instance, the analytics server may retrieve data associated with one or more medical (or other) devices needed for the patient. The analytics server may retrieve data indicating that the patient suffers from a respiratory medical condition. As a result, the analytics server may generate and transmit a query to one or more electronic data sources to identify whether the patient uses/needs a ventilator.

If necessary, the analytics server may also analyze the patient's medical data records to identify the needed patient attributes. For instance, the analytics server may query a database to identify the patient's BMI. However, because many medical records are not digitalized, the analytics server may not receive the patient's BMI value using simple query techniques. As a result, the analytics server may retrieve the patient's electronic health data and may execute one or more analytical protocols (e.g., natural language processing) to identify the patient's body mass index. In another example, if the analytics server does not receive tumor data (e.g., end-points) the analytics server may execute various image recognition protocols and identify the tumor data.

The analytics server may also receive additional data from one or medical professionals. For instance, a treating oncologist may access a platform generated/hosted by the analytics server and may add, remove, or revise data associated with a particular patient, such as patient attributes, treatment attributes, tumor attributes, primary site of treatment, tumor stage, end-point, whether the primary tumor has been extended, and the like. Because tumor staging and the end level attributes are sensitive information that affect patient treatment, these information is typically inputted by the treating oncologist. In some embodiments, an AI model (e.g., a separate AI model that is trained to identify tumor information) may identify this information and the treating oncologist may deny, approve, or revise the predicted results. In another example, the treating oncologist may specifically indicate whether the treatment should be unilateral or bilateral.

The data received by the analytics server (e.g., patient/treatment data) may belong to three categories: numerical, categorical, and visual. Non-limiting examples of numerical values may include patient age, physical attributes, and other attributes that describe the patient. Non-limiting examples of categorical values may include different stages of treatment or disease associated with the patient. Visual data may include medical images representing the patient and his/her treatment regions, such as CT scans or other scans illustrating the patient's tumor.

Another example of a patient attribute may include specific tumor locations. More specifically, this data may indicate the primary tumor location with respect to the patient's centerline. This data may be inputted by the treating oncologist or may be analyzed using various image recognition or segmentation methods executed on the patient's medical images. In some embodiments, this information can also be predicted using the AI model if it is not inputted by the treating oncologist (or otherwise received by the analytics server). Another patient attribute may indicate whether and how close the tumor is to other non-diseased organs. For instance, a tumor to be eradicated may be millimeters away from another organ. This information may change field geometry, as other organs must be avoided.

Another example of a patient attribute may include whether the patient uses prosthesis (e.g., hip or femoral head prosthesis). This attribute may result in a change of the patient's treatment (e.g., patients with these conditions might require a special treatment).

The analytics server may train the AI model using data points associated with the retrieved data. For instance, the analytics server may aggregate the data retrieved into a training dataset. The analytics server may organize the training dataset, such that each data point within the training dataset represents one (or more) attribute described above. For instance, the training dataset may include data tables indicating that different data points and their corresponding data. In an example, a patient may have a set of data points indicating the patient's attributes (e.g., BMI or other physical attributes), the patient's treatment attributes, the patient's organ data, and the like. These data points may correspond to independent variables associated with the patient. These data points are referred to herein as independent variables because each data point indicates an attribute of the patient that does not change based on the patient's treatment. For instance, the patient's weight will remain the same regardless of how the treatment was implemented.

The set of data points may also have a corresponding set of data points indicating how the treatment was previously implemented (e.g., machine attributes or other treatment attributes). These data points are referred to as the dependent variables. The dependent variables represent how the independent variables were applied to an algorithm (or previously analyzed manually by a medical professional to identify the treatment attribute). For instance, the patient's attributes and RTTP data were analyzed to identify the patient's treatment attributes (e.g., how the radiotherapy machine was set up or how the prescribed dosage was delivered to different organs).

The analytics server may train the AI model such that the AI model may analyze the independent variables and predict a dependent variable accordingly. For instance, in a non-limiting example, the analytics server may analyze independent variables to locate a dose-volume histogram (DVH) objectives in IMRT plan optimization. The analytics server may analyze clinical goals as well as clinically approved plans retrieved above to calculate DVH objectives. That is, the analytic server may train the AI model based on previously performed treatments (e.g., data associated with patients and their treatments), such that when executed, the trained AI model can ingest patient attributes and/or treatment attributes dictated by the treating physician to calculate an optimized DVH objectives.

At step 220, the analytics server may determine whether to train the AI model using an exploration or exploitation method. The analytics server may determine whether an epsilon value indicative of a likelihood of exploration and exploitation of training of the artificial intelligence model satisfies a threshold.

The training agent may use a reinforcement learning method to train itself/AI model. As used herein, the "agent" refers to the learner or the trainer (e.g., the analytics server training the AI model or the AI model itself). When training the AI model, the agent may use reinforcement learning techniques to determine when and what data points to use for the training purposes. Therefore, the agent may choose between different actions and may receive a reward based on the chosen action.

Because the agent is using reinforcement learning methods, the agent may choose (e.g., simultaneously) multiple actions and may calculate their corresponding rewards. The agent may then calculate at least one action (or a sequence of actions) that generates the maximum reward. Through multiple iterations, the agent may learn the best actions to take.

In reinforcement learning methods described herein, the agent may interact with a possibly unknown environment (e.g., data used to train the AI model or data associated with a new patient). Therefore, the agent may implement different actions and receive corresponding rewards (e.g., the agent applies an action to the environment and receives new observations and rewards from the environment). The agent may then train itself by choosing the action(s) that provide the highest cumulative set of rewards. Throughout such a sequential decision-making process, the agent learns a policy to maximize the cumulative some the reward. The agent learns how to optimally decide a sequence of actions in order to get the best possible result at the end of the training process.

Throughout the training period, the agent may develop a policy (also referred to as the agent's policy). The policy is a map (expressed in various internal algorithms and mathematical formulas) from the observation space to the action space. An optimal policy guarantees receiving the most (or an optimum level) of rewards by end of the episode. Because the agent contemplates multiple variables, the policy defines how the agent must optimally decide to take an action (or a sequence of actions), such that when rewards is calculated using the multiple variables considered, the agent receives a higher (or the highest) reward. For instance, the agent may sacrifice one reward in order to gain a higher cumulative sum of rewards. Through taking actions and calculating the rewards, the agent may interact with the observation space (e.g., an unknown environment having data points that are not necessarily defined for the agent) and learns from the experience. Specifically, the agent learns (e.g., reconfigures its policy) by taking actions and analyzing the rewards received.

In an example, the agent may train itself using the action-reward system described herein. For instance, the agent receives current observation from the environment ($s_t$). The agent then executes an action ($a_t$) based on its current policy ($\pi_t$) also known as the policy or the agent's policy. Upon executing the action, the agent receives a new observation ($s_{t+1}$), and receives a reward ($r_t$). The agent then updates its policy in order to maximize the cumulative sum of future rewards. In this example, the environment follows the Markov decision process:

$$P[s_{t+1}|s_t]=P[s_{t+1}|s_1, \ldots, s_t]$$

When deciding which action yields the maximum reward, the agent may use an exploration/exploitation methodology. The exploration method, as used herein, allows the agent to train the AI model and improve the AI model's current knowledge about each data point and predict accurate results. In contrast, the exploitation method chooses the greedy action to get the most reward by exploiting the agent's current action-value estimates. Therefore, when an agent explores, it gets more accurate estimates of action-values.

The analytics server may use an epsilon greedy method to train the AI model. Epsilon-Greedy, as used herein, refers to an AI training method that balances exploration and exploitation. In the epsilon greedy method, the agent may first calculate an epsilon value. The epsilon value may refer to the probability of the agent choosing to explore or exploit a data point or an action. Therefore, the epsilon value represents a probability ratio indicating how the agent explores versus how the agent exploits. In an example, the epsilon value may be set as 50% or 0.5. In that example, the agent explores 50% of the time while the agent exploits 50% of the time. In contrast, an epsilon value of 20% or 0.2 indicates that the agent explores 20% of the time while the agent exploits 80% of the time (or vice versa, depending on how the epsilon greedy algorithm is defined).

The analytics server may determine epsilon value (ε) associated with a data point. If the ε value satisfies a threshold, the analytics server may move to the step 230 and generate a random dependent result associated with the analyzed independent data point. For instance, and using an non-limiting example regarding patient attribute as independent data point and treatment attribute (e.g., radiation therapy machine attribute) as a dependent data point, the analytics server may receive a patient attribute and generate a random radio therapy machine attribute associated with the independent data point analyzed. The action taken by the analytics server in step 230 is also referred to herein as the exploration phase.

When the epsilon value does not satisfy the threshold, the analytics server may move to the step 240 (steps 242-248 depicted in FIG. 2B). At step 242, the analytics server may generate a first predicted treatment attribute corresponding to the patient's treatment. The analytics server may execute the agent's policy and generate a first predicted radiation therapy treatment attribute. As discussed above, the AI model may have developed a policy by analyzing the training dataset and iterating through different actions. The analytics server may use the agent's current policy to generate a first predicted attribute. For instance, the analytics server may execute the policy to analyze the patient's RTTP attribute and calculate a predicted dosage to be delivered to an organ (target organ or the patient's organ at risk). For instance, the analytics server may predict treatment attributes (e.g., machine attributes or field geometry) that would lead a particular organ of the patient to receive a particular dosage.

At step 244, the analytics server may execute a predefined model (also referred to herein as the predefined policy) to generate a second predicted radiation therapy treatment attribute. If the epsilon value does not satisfy the threshold, the analytics server may generate a dependent data point based on executing a predefined model. For example, the analytics server may generate a second predicted radiation therapy treatment attribute based on the analyzed data point used to predict the first treatment attribute (step 242).

The predefined model may represent a set of rules expressed in logical sentences. The predefined model may be a computer model configured to receive variables retrieved by the agent (e.g., patient and/or treatment data) and identify treatment attributes (e.g., field geometry, machine attributes, or any data indicating how the patient's treatment should be implemented) associated with a patient's treatment.

The predefined model may comprises of two categories of logical rules. The first type are absolute type of rules that are not weighted and are not dependent upon subjective understanding of the technician (e.g., hard rules). For instance, one rule may indicate that when a medical professional (e.g., the treating oncologist) has indicated a treatment type (e.g., VMAT or IMRT), then the treatment must follow the medical professional's decision. Therefore, this rule does not include any weights or variable to be interpreted using technicians' subjective understanding.

The second type of logical rules may include rules having fuzzy weights and/or variables. For instance, different patient attributes and treatment attributes may be weighted differently to achieve a predicted value that is within acceptable ranges. For instance, a tumor's attribute (e.g., how close the tumor is to another organ or the tumor's position relative to the patient's centerline) may be weighted higher than other patient attributes (e.g., height or BMI). In another example, tumor stage information (e.g., cancer stage) may be weighted higher than tumor's proximity to other organs. For instance, a tumor that has developed dangerously and is in an advanced stage may be treated differently than another tumor that is positioned at the same location but is in early stages (e.g., more advanced tumor might be more aggressively eradicated).

The predefined model may itself be generated using an AI model. For instance, the agent may use a supervised training technique to generate a predefined model/policy, such that when executes the predefined model produces results that are within an acceptable tolerance. In an example, the analytics server generates the predefined model separately and applies the predefined model to improve the agent's policy (step 242). In conventional solutions, the agent's policy produces results that are gradually refined and iteratively corrected as they converge towards an acceptable range. This process is time-consuming and computationally intensive. In contrast, the method 200 may generate a separate predefined model where the results produced by the agent's policy is compared to the results produced by the predefined model, thereby limiting the range of the results used to train the AI model. As a result, the training of the AI model is performed in less time and requires less computation power.

Using the predefined model in conjunction with the agent's policy, the analytics server practically trains the AI model to initially imitate the results generated by the predefined model. Specifically, the analytics server rejects the results generated by the agent's policy that produce less rewards as the predefined model. Given enough iterations, the AI model updates and reconfigures its policy, such that it is as good or better than the predefined model. Therefore, the AI model learns from the predefined model. At that point, the analytics server may stop using the predefined model and only use the agent's policy. Given enough iterations, the AI model may then continuously improve upon the predefined model and predict results that are more accurate (e.g., produce more rewards) than the predefined model. As a result, the trained AI model outperforms human-made plans, the predefined model, and conventionally trained AI models.

The predefined model may refer to any computer model that is configured to produce results that are comparable to the agent's policy. That is, the agent's policy and the predefined model are both configured to generate results (e.g., treatment attributes) that are consistent with the results to be generated by the AI model. For instance, if the agent is training the AI model to generate/predict DVH optimization attributes, then the agent's policy and the predefined model are also configured to generate DVH optimization attributes. Similarly, if the agent is training the AI model to generate/predict radiotherapy machine attributes, then the agent's policy and the predefined model are also configured to generate radiotherapy machine attributes.

In a non-limiting example, the analytics server may use the following logic to generate a predefined model/policy configured to locate the DVH objectives in IMRT plan optimization. The predefined model requires the knowledge of clinical goals as well as clinically approved plans for the treatment cases (e.g., previously implemented treatments) in the training dataset. The analytics server may utilize the following distance measure to compare the state t of the plan-under-optimization with the clinical plan at dose d Gy, specified by a clinical goal, e.g., $V_{d\ Gy} < v$ %, for a given structure (organ):

$$dist(d \mid \text{structure}) = \frac{v_t(d \mid \text{structure})\% - v_o(d \mid \text{structure})\%}{v_o(d \mid \text{structure})\%}$$

For a given structure (organ), $v_o(d)$ % and $v_t(d)$ % denote the volume percent at the dose d Gy corresponding to the clinical plan and state t of the plan-under-optimization respectively. Therefore, the above formula can be also written as:

$$\text{distance} = \frac{\text{Volume of the dose in the current plan} - \text{Volume of the dose in the clinical plan}}{\text{Volume of the dose in the clinical plan}}$$

The analytics server may initialize the predefined model by first analyzing only the planning target volume (PTV) objectives (e.g., indicated by the treating physician). For instance, the analytics server may analyze patient data (e.g., patient's geometry such as relative distance between organs at risk (OARs) and PTV. Then, analytics server may add OAR objectives/details at different dose levels specified by clinical goals while preserving the volume level corresponding to the current state of the plan.

With each iteration of training, the analytics server may iteratively repeat the following steps until a stopping criterion is met. First, the analytics server may calculate the signed distance for all the DVH objectives. Then the analytics server may choose the objective with the maximum relative distance. Depending on the type of this objective, the analytic server may choose actions as follows:

If the type of the objective is PTV LOWER, then the analytics server may move the objective (e.g., revise the value of the objective) using a predetermined amount (β) towards a higher dose. As a non-limiting example, PTV LOWER may indicate that a dosage of 98% of the target organ volume is greater than 100% of the prescribed dosage (e.g., $V_{100\%Rx} > 98\%$). However, these variables can be revised by a system administrator.

If the type of the objective is PTV UPPER, then the analytics server may move the objective (e.g., revise the value of the objective) using a predetermined amount (β) towards the lower dose. As a non-limiting example, "PTV UPPER" may indicate that a volume of the target organ at 110 percent of prescription dose is less than 2% of total volume (e.g., $V_{110\%Rx}$<2%). However, these variables can be revised by a system administrator.

If the type of the objective is OAR UPPER, then the analytics server may move the objective (e.g., revise the value of the objective) using a predetermined amount (a) towards the lower volume. As a non-limiting example, "OAR UPPER" may indicate that volume of organ at 65 Gy should be (or is) less than 25% of total OAR volume (e.g., $V_{65Gy}$<25%). However, these variables can be revised by a system administrator.

As described above, the analytics server may continue the iterations until a stopping criterion is met. A non-limiting example of the stopping criterion is as follows:

All the distance values are smaller than or equal to zero and/or the mean of the distance values over all the objectives does not decrease any further by taking new actions (e.g., the values are converging). In this way, the performance of the predefined model is equal to or better than the clinical plan at the clinical goals. Once the stopping criterion is satisfied, the analytics server implemented the predefined model within the AI training method 200.

The analytics server may iteratively refine the predefined model by using the predefined model in the training scheme described herein (method 200). For instance, the analytics server may have previously generated the predefined model and may retrieve and execute the predefined model when executing the step 246. As discussed above, predefined models may be configured to predict specific attributes. For example, the above-described predefined model may predict DVH objectives. Therefore, the analytics server may first identify an appropriate predefined model that corresponds to the attributes to be predicted by the AI model (to be trained). For instance, if the analytics server is training the AI model to predict field geometry, then the analytics server may generate and/or retrieve a predefined model configured to output/predict field geometry.

The analytics server may execute the predefined model by inputting the patient attributes collected from various electronic data sources (step 210). For instance, the analytics server may execute code corresponding to the predetermined rules codified within the predefined model to identify various treatment attributes.

Even though some embodiments discussed herein describe a single predefined model, the analytics server may use multiple predefined models. For instance, the analytics server may analyze multiple predefined models and select a most relevant predefined model and utilize the selected predefined model for training purposes. As non-limiting example, the data repository may include multiple predefined models where each predefined model is associated with a particular clinic. When training the AI model for a particular clinic, the analytics server may select a predefined model that corresponds to the clinic. As a result, the AI model may be trained such that the results are uniquely tailored towards the clinics need.

At step 246, the analytics server may apply the first predicted or the second radiation therapy treatment attribute and the radiation therapy treatment attribute. As described above, the predefined model may be a codified set of rules that are used to verify the accuracy of the results generated using the methods and systems described herein. Specifically, the analytics server may compare the results generated by the agent (step 242 and 244) and select the value that produces the most rewards. The analytics server may compare the random treatment attribute value generated at step 220 and the predicted treatment attribute generated in step 242 and/or 244.

As a non-limiting example, in Deep Q-learning (DQN) method of training reinforcement learning agents, deep neural networks are used to approximate action-value functions (Q-functions) for a given state for every possible action. The function Q(S, A) specifies how much reward we expect until the end of the episode (e.g., if in state S, the agent chooses action A). Therefore, the analytics server may utilize these methods to compare the results generated in steps 230, 242, and/or 244. Particularly, the agent may determine whether the agent's policy or the predefined model generate attributes that produce higher rewards. The agent may also compare the agent's policy and/or the predefined model to the randomly generated value at step 230. The agent may then utilize the action that yield the most rewards in training the AI model.

With regard to calculating rewards associated with different DVH objectives, in some embodiments, the reward calculations may executed, such that certain organs are weighted differently than other organs. The reward calculation for an action may indicate whether the dosage is appropriately administered to the target organ. However, the target organ may also include a cost function that indicates how the dosage is also administered to other OARs. Therefore, the reward may be represented by a combination of these two elements. However, the analytics server may weigh the cost to different OARs differently. For instance, the patient's spinal cord may receive a higher weight than the patient's rectum. As a result, the cost for dosage received at the patient's spinal cord is higher than the same dosage delivered the patient's rectum. As a result, the AI model will be trained in a customized manner, such that administering dosage to the patient's spinal cord is minimized more than the patient's rectum. Different weights for OARs can be modified by a system administrator and the weight values and preferences for different OARs can be determined by a treating physician or a medical professional.

In some configurations, the analytics server may learn the weights and preferences of different OARs based on previously administered and implemented treatments. For instance, the analytics server may learn (using the methods described herein) that the agent's action must comply with various patterns identified within the previously administered treatments where the actions show a proclivity towards avoiding certain OARs more than other OARs.

At step 248, the analytics may iteratively repeat training the artificial intelligence until the existing policy satisfies an accuracy threshold. The analytics server (agent) may continue training the AI model until a predetermined threshold is met.

The threshold may represent any training metric predefined by a system administrator. For instance, the analytics server may determine whether recall or precision of the trained AI model satisfies a threshold. In another example, the analytics server may compare the first and/or second predicted treatment attributes with a ground truth data and stop the training when the difference between those values satisfy a threshold (e.g., are less than a predetermined amount).

In some configurations, the analytics server may iteratively repeat training the artificial intelligence model until an optimum policy is reached. For instance, the agent continues training the AI model until the agent's policy is optimum. As used herein, an agent's policy is optimum if it achieves the maximum possible sum of cumulative rewards within a predetermined time period (e.g., by the end of the training period or any other time selected by the agent or a system administrator). As discussed above, the agent may use various methods of calculating the rewards, such as DQN techniques.

The analytics server/agent may regularly evaluate the agent's policy (e.g., values generated in step 242) in maximizing the cumulative sum of rewards until the agent's policy is at least as good as the predefined model (values generated as a result of execution of the predefined model in step 244). At this point, the predefined model is swapped by the agent's policy and conventional training continues until reaching an optimum policy. For instance, the analytics server instructs the AI model to no longer generate any attributes using the predefined model when the agent's policy satisfies a predetermined valuation threshold (e.g., reaches optimum).

The analytics server may then execute the trained AI model to generate various treatment attributes. When executed, the trained AI model may produce results that can be displayed on an electronic device and/or the radiation therapy machine. Non-limiting examples of results generated and/or outputted by the AI model may include treatment plans including fluence maps and/or DVH curves.

Additionally or alternatively, the analytics server may communicate with the radiation therapy machine and/or a host server operatively in communication with the radiation therapy machine to modify and revise the radiation therapy machine's configurations. For instance, the analytics server may determine field geometry for a patient. The analytics server may then identify a radiation therapy machine implementing the patient's treatment. The analytics server also determines the patient's field geometry using methods and systems described herein (via executing the trained AI model). The analytics server then instructs the radiation therapy machine (e.g. by transmitting executable instruction files to the host server) to adjust its configurations according to the identified field geometry. For instance, the analytics server may instruct the radiation therapy machine to adjust its couch angles according to the calculated/optimized field geometry.

In addition to the AI training methods and systems described herein, the analytics server may also monitor various end-users interactions with the identified data to improve the results by revising and retraining the AI model. The analytics server may monitor the electronic device viewing the field geometry to identify interactions between the end user and the electronic device while the electronic device is outputting the results. Based on the end-users interactions (e.g., approval, denial, and/or modification of the results), the analytics server may then revise and retrain the AI model.

When the user performs an activity on the electronic platform, the analytics server may track and record details of the user's activity. For instance, when a predicted result is displayed on the user electronic device, the analytics server may monitor to identify whether the user has interacted with the predicted results by editing, deleting, accepting, or revising the results. The analytics server may also identify a timestamp of each interaction, such that the analytics server records the frequency of modification, duration of revision/correction.

The analytics server may utilize an application-programming interface (API) to monitor the user's activities. The analytics server may use an executable file to monitor the user's electronic device. The analytics server may also monitor the electronic platform displayed on an electronic device via a browser extension executing on the electronic device. The analytics server may monitor multiple electronic devices and various applications executing on the electronic devices. The analytics server may communicate with various electronic devices and monitor the communications between the electronic devices and the various servers executing applications on the electronic devices.

In some embodiments, the analytics server may monitor the data packages received and sent by each electronic device to monitor the content of what is displayed/executed/modified on the electronic device. The communication may take any suitable form. For example, the electronic device may execute an application (e.g., browser extension) having an executable file that enables a user to navigate to the electronic platform (e.g., web site).

The analytics server may use several techniques to track user's activities on the electronic device, such as by tracking browser cookies and/or screen-scraping protocols. In another example, the analytics server may track the user activity by periodically retrieving user's web browser cookies. The analytics server may transmit cookies to a system database where they can be analyzed (e.g., in batches) to identify user activities.

In some configurations, the analytics server may monitor the electronic device using an executable file (application) installed as a browser extension. The browser extension (executable file) may be executing as a background process of the electronic device. For instance, the browser extension may be transparent to the user operating the electronic device. In this way, the analytics server is able to monitor the user's activities without disturbing the user and/or obfuscating the display screen of the electronic device. In some embodiments, the analytics server may activate a monitoring module (e.g., browser extension or executable file) upon outputting the results on the electronic platform.

The analytics server may use the data collected/monitored to train the AI model and improve its predicted results. In order to train the AI model, the analytics server may generate new training datasets.

The analytics server may monitor whether an end user accepted the predicted results. The analytics server may generate a metric corresponding to a frequency that a certain predicted result was accepted, denied, or revised. If the predicted results were accepted, the analytics server assumes that the predicted results were satisfactory to the end user. If the user revised the predicted results, the analytics server assumes that they were partially satisfactory to the user. Finally, if the user denied the predicted results, the analytics server assumes that they were completely unsatisfactory. The analytics server may also generate a metric for how frequently predicted results generated by a model is accepted, revised, and/or denied.

As described above, when a user revises a predicted result, the analytics server monitors the revision performed by the user. In some embodiments, the analytics server displays a predicted result on the electronic platform. However, the users feel the need to perform minor corrections before they are satisfied with the results. The analytics server may monitor this correction and generate training datasets accordingly. For instance, the analytics server may monitor a time duration that each user spent correcting the predicted results. The analytics server may assume that a higher this monitored time duration corresponds to more inaccurate the results.

In some embodiments, the analytics server may also monitor the corrections themselves and use this data to train the AI model. For instance, training and revising the AI model may be proportionally implemented based on the end-users modifications. For instance, the analytics server may generate a training dataset that includes the amounts of corrections inputted by the user (e.g., whether the user revised the results by 10% or 80%).

The analytics server may always display a prompt requesting users' feedback. In some embodiments, the analytics server may display the prompt based on a predetermined frequency (e.g., 50% of instances where a predicted result is displayed). Furthermore, the analytics server may select the users receiving the prompt based on predetermined rules. For instance, the analytics server may select the users randomly. In some configurations, the predetermined rules may require the analytics server to display the prompt for users who satisfy a certain threshold (e.g., only for users who have three or more years of experience or only treating oncologist and not technicians).

The analytics server may train the AI model using the above-described training datasets. For instance, the analytics server may use one or more of the following AI approaches to train the AI model: regression, classification, clustering, dimensionality reduction, ensemble methods, neural nets and deep learning, transfer learning, reinforcement learning, and the like. In some embodiments, the analytics server may periodically train the AI model. For instance, the analytics server may collect/monitor user interactions and store the corresponding data. The analytics server may then use a predetermined frequency (e.g., once a month or once a week) to train the AI model using the stored training datasets. A system administrator can modify the frequency of the batch training.

Additionally or alternatively, the analytics server may train the AI model when the model produces results that receive feedback that satisfies a threshold. For instance, the analytics server trains the model when the results outputted on the electronic platform receive a feedback (e.g., thumbs down or modification/revision of the results by the users) more frequently than a predefined threshold (e.g., 40% of time).

Additionally or alternatively, the analytics server may train the model based on a customized (predetermined) segmentation of training data and/or users. For instance, the analytics server may segment the training data before training the AI model. The analytics server may train the AI model in a customized and segmented manner that is meaningfully tethered to the end users' needs. In a non-limiting example, the analytics server may train the AI model based on feedback received from a selection of users (e.g., users who work at a particular clinic or users who satisfy a certain score). As a result, the analytics server may customize the AI model for a particular clinic. This training method allows the AI model to adapt to the particular clinic and produce results that are more acceptable to the users within that clinic.

The method and systems described herein allow a central server, such as the analytics server or the agent discussed herein, to use reinforcement learning techniques to train and artificial intelligence model. Specifically, the methods and systems described herein can augment the reinforcement learning techniques using supervised learning methods. For instance, the supervised learning may be used to pre-train the agent (e.g., the predefined model), to reduce training time and computational power needed to train the AI model. The methods and systems described herein increase training efficiency by generating a predefined model (a set of logical rules), which receives the same observations as the reinforcement learning agent and outputs a reasonable action (e.g., the action does not need to be optimal however is within predefined reasonability thresholds because the action is dictated by the pre-defined policy). The policy may be pre-generated using clinical plans and may be revised by a system administrator. For instance, a system administrator can revise the predefined model, such that the training is modified or customized based on the system administrator's desires.

Figure 3:
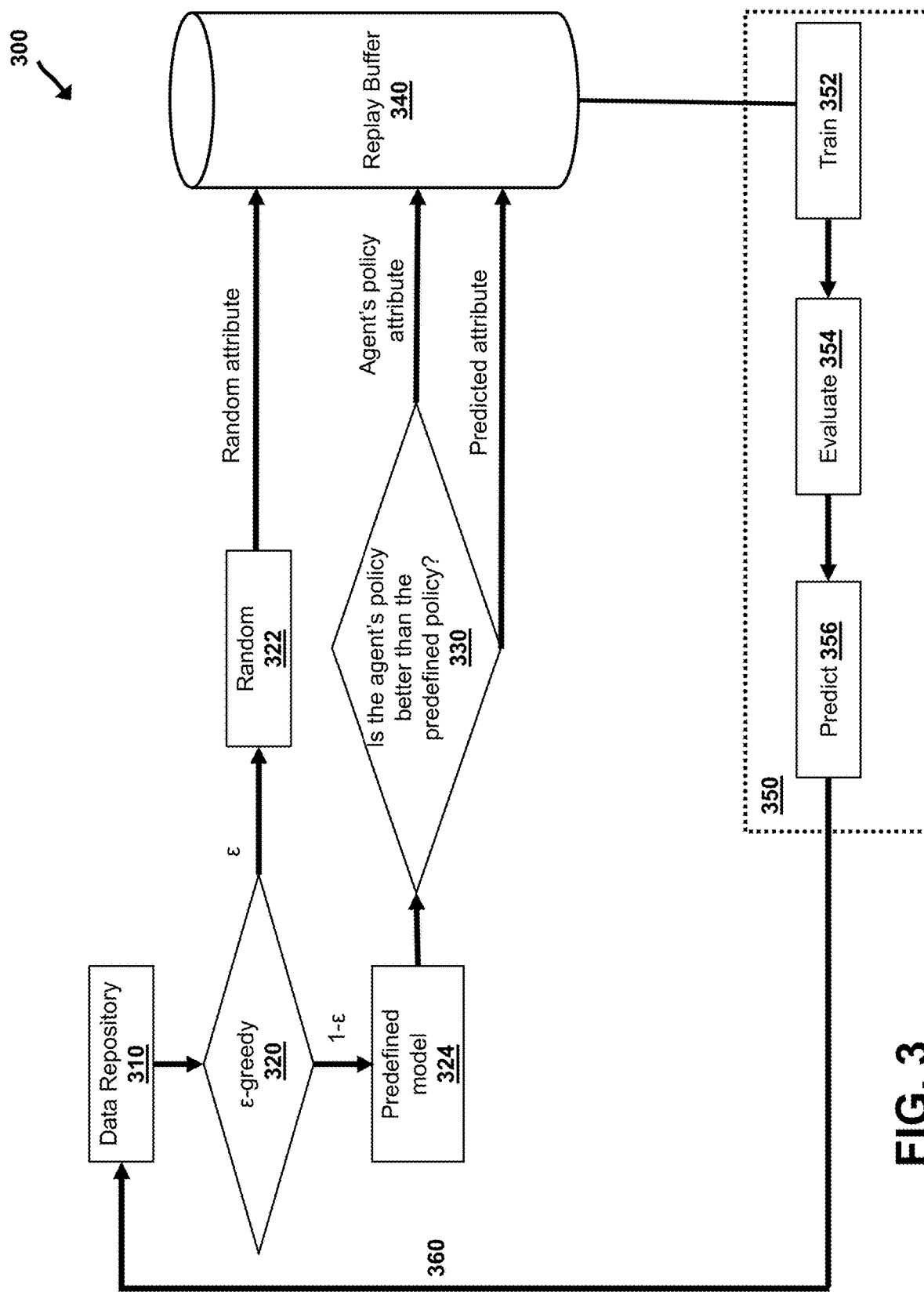
FIGS. 3-5 illustrate a flow diagram of a process executed in an AI-enabled RTTP optimization system, according to an embodiment.
Figure 4A:
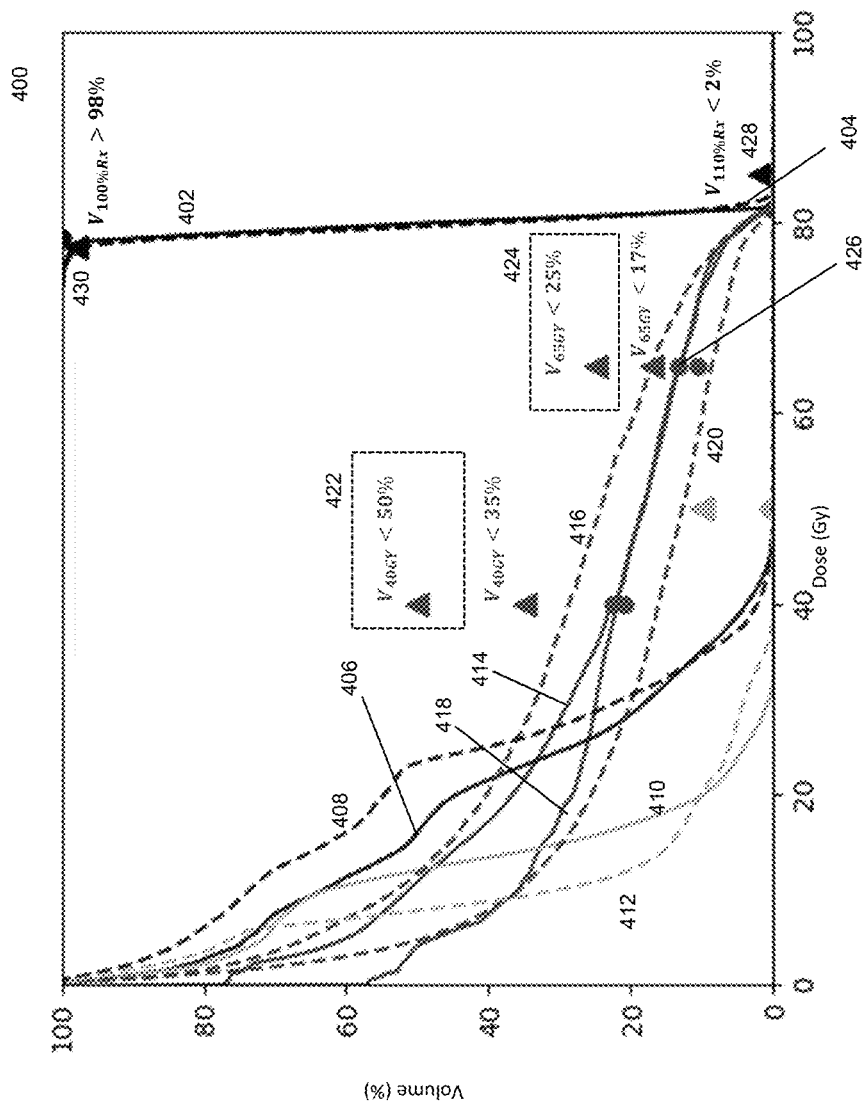
Figure 4B:
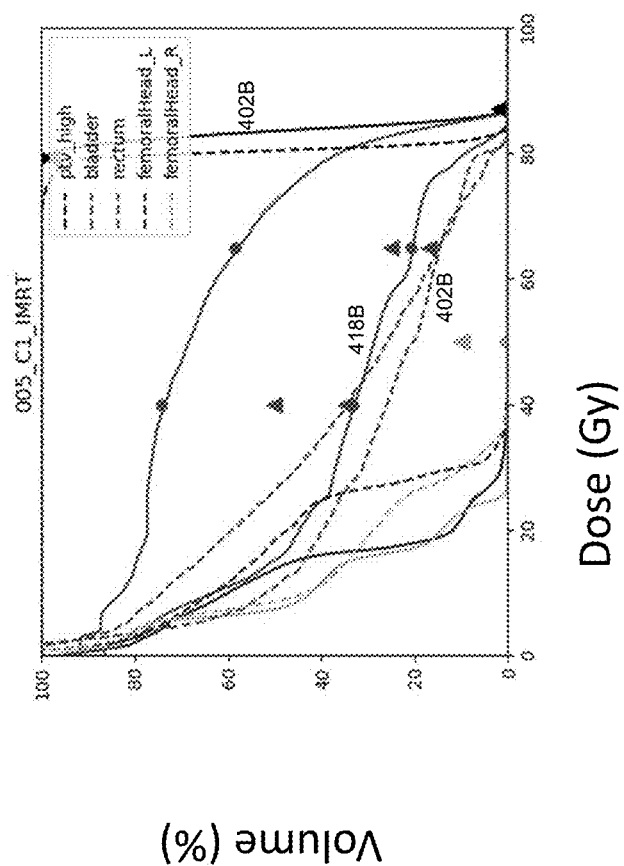
Figure 4C:
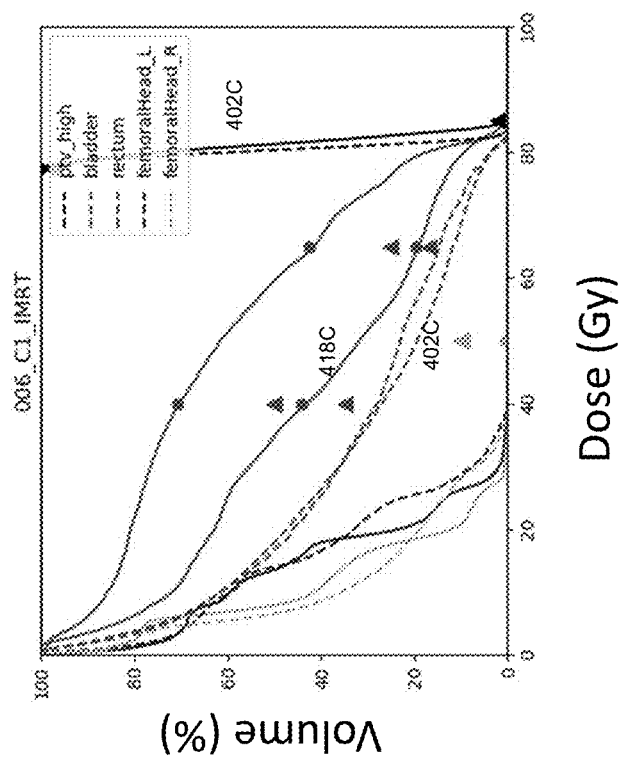
Figure 4D:
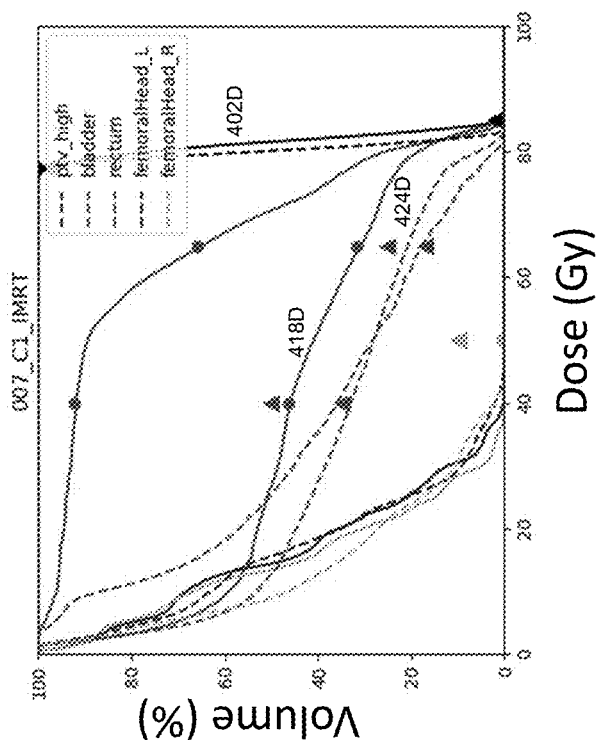
Figure 5:
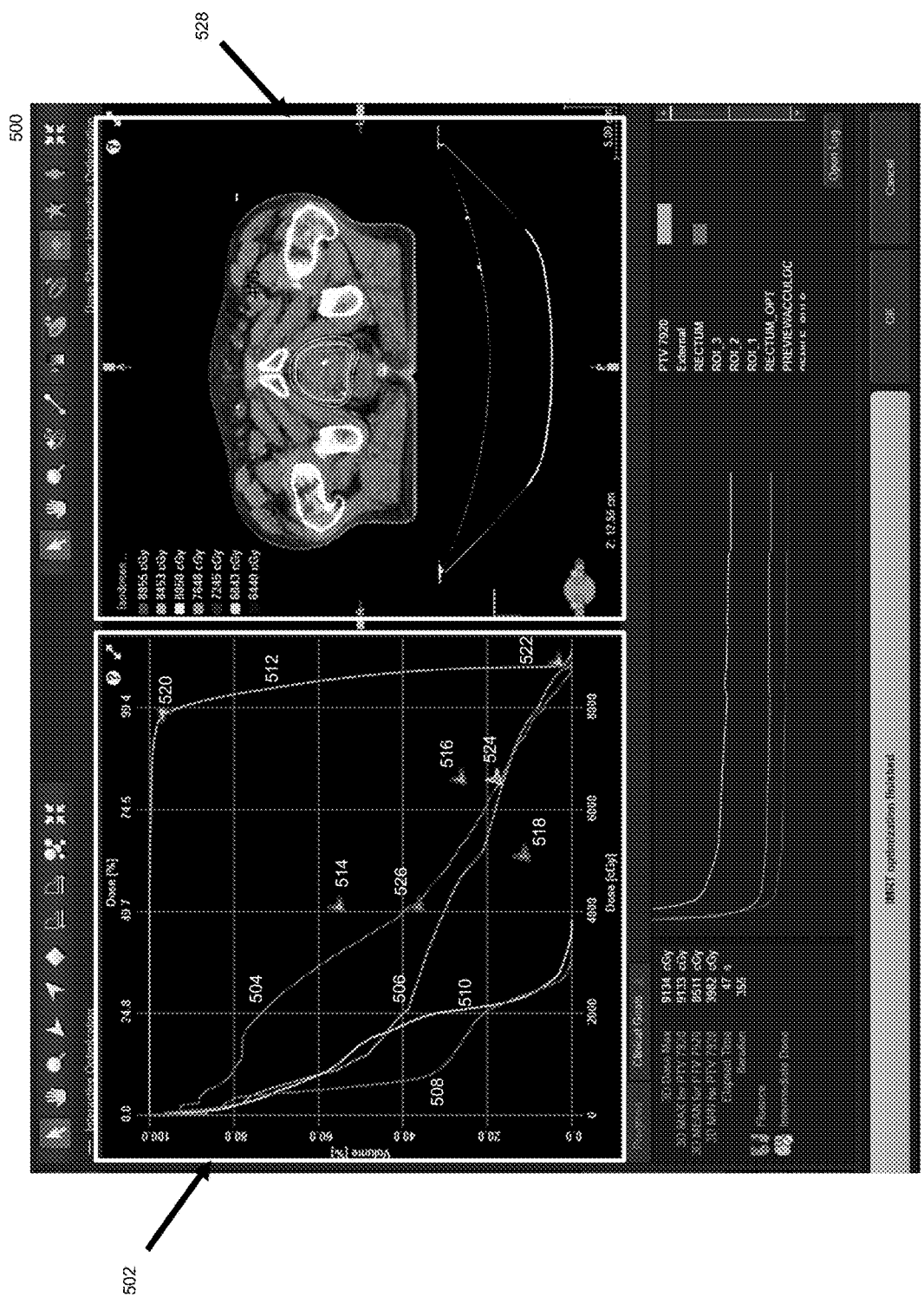

Referring now to FIGS. 3-5, non-limiting examples of a workflow utilizing the methods and systems described herein is illustrated. In this non-limiting example 300, the analytics server trains an AI model using training data stored within the data repository 310. The analytics server may train the AI model to predict and optimize DVH objectives. That is, the trained AI model may be executed where the trained AI model ingests patient information and the patient's treatment plan (e.g., target organ, dosage to be delivered to the target organ, geometry associated with the patient's target organ and OARs). As a result, the analytics server trains the AI model using a predefined model similar to the predefined example described in step 244 (FIG. 2).

The data repository 310 may include data associated with previously performed treatments. For instance, the data repository 310 may include data points associated with RTTP and all data points corresponding to clinic data (e.g., how the RTTP was previously implemented in different clinics). The analytics server may iteratively perform the method 300 for different data points within the data repository 310. The analytics server may continue the training until a predetermined threshold has been satisfied. For instance, the analytics server may train the AI model until the recall, precision, or any other value indicating the accuracy or efficiency of the AI model reaches a predetermined level.

To train the AI model, the analytics server may retrieve a data point representing an independent attribute of a previously implemented radiation therapy treatment. The analytics server may first determine whether an exploration action or an exploitation action is needed. The analytics server may generate an epsilon value. For instance, upon retrieving the independent attribute, the analytics server may apply an epsilon greedy algorithm and determine whether an exploration or an exploitation algorithm must be applied (320). If the epsilon value indicates an exploration, the analytics server may generate a random attribute corresponding to the retrieved independent attribute (322). This "action" produces a random attribute. The analytics server may then transmit the random attribute to the replay buffer 340, such that (when aggregated with other values), the data point can be used for training the AI model.

If the epsilon value indicates an exploitation, the analytics server may apply a predefined model (324) and generate a predicted attribute. The analytics server may also generate an agent's policy attribute using the agent's policy.

The analytics server may then compare the agent's policy attribute and the predicted attribute generated via the predefined model or predefined policy (330). If the agent's policy attribute is better, the analytics server may store agent's policy attribute within the replay buffer 340. In contrast, if the predicted attribute is better, the analytics server may store the predicted attribute within the replay buffer 340. In some configurations, the analytics server may compare the random attribute, the agent's policy attribute, and the predicted attribute, thereby the analytics server may only store one of the attributes that produces the most rewards.

The analytics server may use a supervised learning scheme to imitate the predefined model. For instance, the analytics server may incorporate (using the methods described herein) the pre-trained predefined model in a conventional reinforcement learning training scheme depicted herein. The analytics server may continue training until the agent's policy reaches an optimum policy through exploration. When the agent's policy is better than the predefined model, the analytics server may switch from using the predefined model to using the agent's policy. When comparing two policies, policy A is better than policy B (e.g., $\pi_A > \pi_B$) if, policy A achieves a bigger sum of cumulative rewards than policy B, until the end of the episode. Therefore, the methods described herein use supervised learning to augment the reinforcement learning.

The analytics server may iteratively repeat this process until the replay buffer 340 has enough data points to effectively and efficiently train the AI model. In some embodiments, the data stored within the replay buffer 340 may be deleted after the AI model is trained. In some other embodiments, the data within the replay buffer 340 may be stored for training AI models and or other purposes, such as model validation. For instance, the analytics server may iteratively perform the method 300 and store various attributes within the replay buffer 340. When the analytics server receives a request to train a second AI model, the analytics server may directly retrieve the data from the replay buffer 340 instead of the data repository 310. As a result, the analytics server may train the second AI model more efficiently and without iteratively revising and optimizing the data repository 310.

The analytics server may train the AI model using data points stored within the replay buffer (352). The analytics server may also evaluate the AI model using various existing evaluation techniques (354). For instance, the analytics server may determine recall precision or any other attributes of the AI model that indicates a level of accuracy for the predicted values (356). The analytics server may train, evaluate, and predict the AI model using various techniques and existing methodologies (350). In some configurations, the analytics server may perform the step 350 by utilizing third-party services.

If the AI model is trained (e.g., if the analytics server evaluates that the AI model has at least one attribute that satisfies a predetermined efficiency and or accuracy threshold), the analytics server stops the training. However, if the threshold is not reached, the analytics server may repeat the method 300. As described above, analytics server may repeat this iteration until the AI model reaches an acceptable efficiency and/or accuracy tolerance (360).

When trained, the analytics server may receive new patient data and may execute the trained AI model to predict an optimum dose distribution for the patient. Referring now to FIG. 4A, chart 400 depicts a non-limiting example of a dose distribution among a patient's different organs. Each solid line (e.g., 402, 406, 410, 414, and 418) depicted in the chart 400 indicates how different organs receive treatment dosage in accordance with the AI model trained using the methods described herein. Moreover, each dashed line (dashed lines 404, 408, 412, 416, and 420) depicted in the chart 400 indicates a clinical plan (or a clinically approved plan) for an organ.

Accordingly, each solid line has a corresponding dashed line where each pair of lines corresponds to an organ. In the chart 400, line 402 and its corresponding dashed line 404 correspond to a tumor within the patient's prostate. The prostate represents the target organ. The line 406 and its corresponding dashed line 408 correspond to the patient's left femoral head. The line 410 and its corresponding dashed line 412 correspond to the patient's right femoral head. The line 414 and its corresponding dashed line 416 correspond to the patient's rectum. The line 418 and its corresponding dashed line 420 correspond to the patient's bladder. The clinical plan for this patient requires a 77.4 Gy dosage administered to the patient's prostate. The analytics server may train the AI model using the methods and systems described herein to administer and deliver the clinically required dosage to the patient's prostate while minimizing the dosage administered to the patients OARs (bladder, rectum, right femoral head, and left femoral head).

Each triangle depicted within the chart 400 identifies a clinical goal. The patient's RTTP may require more than one clinical goals for one or more OARs. For instance, the patient's treatment requirements (set by a treating physician or retrieved from other clinical protocols) may limit the dosage received by the bladder using two clinical goals (422 and 424). Each clinical goal may indicate a maximum amount of dosage that can be received by a particular OAR. For instance, the clinical goal 422 indicates that 50% of the patient's bladder must not receive more than a 40 Gy dosage. Similarly, the clinical goal 424 indicates that 25% of the patient's bladder must not receive more than a 65 Gy dosage.

Similarly, the patient's treatment plan may also include clinical plans for different OARs. For instance, the dashed line 420 indicates approved dosages at different volumes of the patient's bladder. The trained AI model must calculate how to deliver the appropriate dosages to the target organ while the dosage received by each OAR remains below its respective clinical goal (depicted by triangles).

Each circle depicted within the chart 400 identifies a DVH objective. For instance, the DVH objective 426 indicates the percentage volume and the dosage to be administered to the patient's bladder. The trained AI model may optimize the DVH objectives, such that they are consistent with the approved clinical plans (e.g., depicted dashed lines) and below the clinical goals (e.g., depicted using triangles). Therefore, in the non-limiting example depicted within the chart 400, the AI models objective is to administer dosage to the patient's prostate, such that the delivery is within the ranges indicated by the clinical goals 430 and 428 and is further consistent with the clinically approved plans depicted as dashed lines. The AI model's goal is to also minimize the inevitable delivery of the dosage to the patient's OARs.

In order to train the AI model and achieve the results depicted in the chart 400, the analytics server may first initialize the training using only with PTV objectives (e.g., objectives regarding how the dosage should be delivered to the patient's prostate). This provides information on the patient's geometry. As expected and seen in FIGS. 4B-D, the dosage delivered to the prostate (lines 402B-D) comply with the PTV requirements. However, the OARs do not comply with the clinical goals or clinical plans. For instant, line 418B (depicting dosage received by the patient's bladder) indicates that the dosage is higher than the clinical plan (line 420B). Similarly, as depicted in FIG. 4C, line 418C (depicting dosage received by the patient's bladder) indicates that the dosage is higher than the clinical plan (line 420C). Moreover, as depicted in FIG. 4D, line 418D (depicting dosage received by the patient's bladder) indicates that the dosage is higher than the clinical goal (line 424D). After a few iterations, the AI model may then set the OAR objectives at the dose levels specified by clinical goals, but volume levels corresponding to the current state of the plan. With enough iterations, the analytics AI model reaches the DVH curves depicted in the chart 400. As depicted, the plan generated by the AI model closely resembles the clinically approved plan while not violating the clinical goals.

When the AI model is trained, the analytics server may execute the train AI model to optimize treatment attributes and may display the results on a graphical user interface (GUI) displayed on the user's computer. For instance, and referring to the GUI 500 depicted in FIG. 5, the analytics server may display the chart 502 that includes an optimized fluence map. Similar to the chart depicted in FIG. 4, the chart 502 includes different lines indicating dosage delivery to different organs. For instance, line 512 indicates the delivery to the target organ and lines 504, 506, 508, and 510 depict how dosage will be delivered to different OARs.

The chart 502 may also include clinical goals that indicate a maximum dosage delivery allowable for each organ. For instance, the clinical goals 520 and 522 indicate the maximum allowable dosage delivery to the target organ. The clinical goals 514 and 516 indicate a maximum allowable dosage delivery amount for the organ depicted by the line 506; the clinical goals 524 and 526 may indicate a maximum dosage allowed for the organ depicted in the line 504. Similarly, the clinical goal 518 indicates a maximum dosage allowed to be delivered to the organ depicted in line 508. As depicted, all doses delivered to the target organ and the patient's OARs are below the clinical goals.

The GUI 500 also includes the graphical component 528 where various patient's organs including the target organ and the OARs are depicted. The end user may review the dosage delivery and may approve or deny the optimize plan. For instance, the end-user may interact and change the dosage delivered to a particular organ at a particular volume/location, as needed.

Using the methods and systems described herein, an agent (e.g., AI model), may first imitate a predefined computer model (using supervised learning) in order to quickly learn the basic rules of the plan generation process (e.g., how to produce a policy that generates results that will produce higher rewards). After the agent has learned to imitate the predefined computer model, the training still continues until reaching an optimal policy in generating high quality plans in a fast rate.

The agent continues to interact with the plan generation system (the environment) following the policy it has learnt from the predefined computer model. The agent further develops its policy until reaching an optimal policy (e.g., maximizing the cumulative sum of the rewards the agent receives until the end of the episode). For a given patient, an episode starts with initializing the plan generation system and ends with generating a clinically acceptable plan (a quality plan) as quickly as possible. During the episode the agent is interacting with the environment through a sequential decision-making process to generate the plan. When trained, the agent can outperform any other existing plan generation methods including the human made plans.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for

What we claim is:

1. A method of training an artificial intelligence model using reinforcement learning, the method comprising:
iteratively training, by a server, the artificial intelligence model using a training dataset comprising a set of radiation therapy treatment attributes associated with previously performed radiation therapy treatments to predict a corresponding set of radiation therapy treatment attributes, wherein with each iteration the server:
applies a random radiation therapy treatment attribute corresponding to the radiation therapy treatment attribute associated with previously performed radiation therapy treatments when an epsilon value indicative of a likelihood of exploration and exploitation training of the artificial intelligence model satisfies a threshold; and
when the epsilon value does not satisfy the threshold, the server:
generates, using an existing policy, a first predicted radiation therapy treatment attribute, and
generates, using a predefined computer model, a second predicted radiation therapy treatment attribute,
wherein the server applies one of the first predicted radiation therapy treatment attribute or the second predicted radiation therapy treatment attribute that is associated with a higher reward,
wherein the server iteratively repeats training the artificial intelligence model until the existing policy satisfies an accuracy threshold.

2. The method of claim 1, further comprising:
executing, by the server, the trained artificial intelligence model.

3. The method of claim 1, wherein the epsilon value is received from a system administrator.

4. The method of claim 1, wherein the server compares the first predicted radiation therapy treatment attribute with the second predicted radiation therapy treatment attribute.

5. The method of claim 1, wherein the server trains the existing policy based on the predefined computer model using a supervised training method.

6. The method of claim 1, wherein the server revises the epsilon value, such that a likelihood of generation of the first or second predicted radiation therapy treatment attribute is higher than generation of the random radiation therapy treatment attribute.

7. The method of claim 1, wherein the server revises the epsilon value, such that a likelihood of generation of the first or second predicted radiation therapy treatment attribute is lower than generation of the random radiation therapy treatment attribute.

8. The method of claim 1, wherein the predefined computer model is received from a system administrator.

9. The method of claim 1, wherein the predefined computer model is specific to a clinic.

10. The method of claim 1, wherein the predefined computer model is specific to optimizing a dose-histogram volume calculation.

11. A system for training an artificial intelligence model using reinforcement learning comprising:
one or more processors; and
a non-transitory memory to store computer code instructions, the computer code instructions when executed cause the one or more processors to:
iteratively train the artificial intelligence model using a training dataset comprising a set of radiation therapy treatment attributes associated with previously performed radiation therapy treatments to predict a corresponding set of radiation therapy treatment attributes, wherein with each iteration the one or more processors:
apply a random radiation therapy treatment attribute corresponding to the radiation therapy treatment attribute associated with previously performed radiation therapy treatments when an epsilon value indicative of a likelihood of exploration and exploitation training of the artificial intelligence model satisfies a threshold; and
when the epsilon value does not satisfy the threshold, the one or more processors:
generate, using an existing policy, a first predicted radiation therapy treatment attribute, and
generate, using a predefined computer model, a second predicted radiation therapy treatment attribute,
wherein the one or more processors apply one of the first predicted radiation therapy treatment attribute or the second predicted radiation therapy treatment attribute that is associated with a higher reward,
wherein the server iteratively repeats training the artificial intelligence model until the existing policy satisfies an accuracy threshold.

12. The system of claim 11, wherein the computer code instructions when executed further cause the one or more processors to execute the trained artificial intelligence model.

13. The system of claim 11, wherein the epsilon value is received from a system administrator.

14. The system of claim 11, wherein the one or more processors compare the first predicted radiation therapy treatment attribute with the second predicted radiation therapy treatment attribute.

15. The system of claim 14, wherein the one or more processors train the existing policy based on the predefined computer model using a supervised training method.

16. The system of claim 11, wherein the one or more processors revise the epsilon value, such that a likelihood of generation of the first or second predicted radiation therapy treatment attribute is higher than generation of the random radiation therapy treatment attribute.

17. The system of claim 11, wherein the one or more processors revise the epsilon value, such that a likelihood of generation of the first or second predicted radiation therapy treatment attribute is lower than generation of the random radiation therapy treatment attribute.

18. The system of claim 11, wherein the predefined computer model is received from a system administrator.

19. The system of claim 11, wherein the predefined computer model is specific to a clinic.

20. The system of claim 11, wherein the predefined computer model is configured to optimize a dose-histogram volume calculation.

* * * * *